United States Patent
Beane

[11] Patent Number: 5,116,333
[45] Date of Patent: May 26, 1992

[54] BIPOLAR HANDSWITCH ADAPTER

[75] Inventor: Richard M. Beane, Hingham, Mass.

[73] Assignee: Kirwan Surgical Products, Inc., Rockland, Mass.

[21] Appl. No.: 608,552

[22] Filed: Nov. 2, 1990

[51] Int. Cl.⁵ .............................. A61B 17/36
[52] U.S. Cl. ........................ 606/51; 606/42; 606/52
[58] Field of Search .............. 606/28, 29, 34, 37, 606/39–42, 45–52; 200/61.58 R

[56] References Cited

U.S. PATENT DOCUMENTS 4,041,952  8/1977  Morrison, Jr. et al. ............ 606/51
4,370,980  2/1983  Lottick ............................. 606/42

Primary Examiner—Stephen C. Pellegrino
Assistant Examiner—Steven J. Shumaker

[57] ABSTRACT

This is a hand switch adapter for use with two prong bipolar forceps. It utilizes a reed spring for energizing a circuit which in turn activates the main circuit.

2 Claims, 1 Drawing Sheet 5,116,333

1

BIPOLAR HANDSWITCH ADAPTER

SUMMARY OF THE INVENTION

This is a hand switch adapter for use with bipolar forceps, the hand switch adapter comprising a handswitch adapter base and an adapter extension. The handswitch adapter base is formed of an electrically nonconductive material and includes a tubular handswitch adapter connector open at one end and extending from the handswitch adapter base in integral right angle relation thereto. The adapter extension is formed of a coaxial, electrically conductive material and engaged to the open end of the handswitch adapter connector. The adapter extension has a free end remote from the handswitch adapter connector which includes a reed microswitch. Tthe handswitch adapter base has a front face and a rear face. A pair of spaced through holes are formed therethrough and a terminal pin extending from the rear face in a direction opposite from that toward which the adapter extension extends.

BRIEF DESCRIPTION OF THE DRAWINGS

Further details are explained below with the help of the example(s) illustrated in the attached drawings in which.

DESCRIPTION OF THE PREFERRED EMBODIMENT(S)

Figure 1:
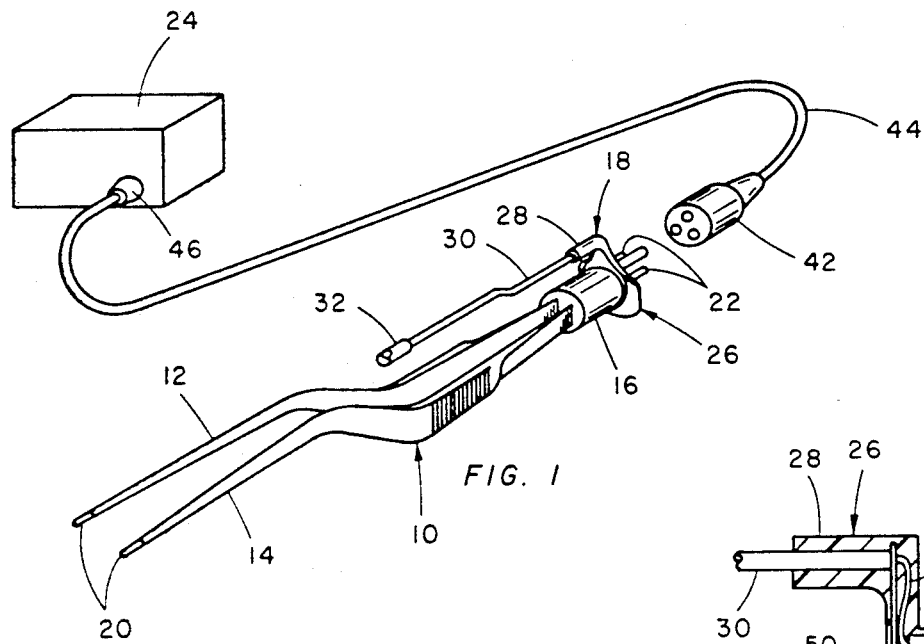
FIG. 1 is a perspective view of the hand switch system showing the bipolar handswitch adapter according to the present invention.
Figure 6:
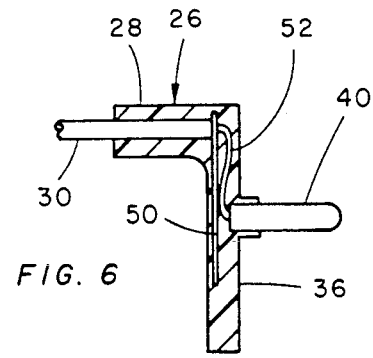
FIG. 6 is a sectional view of the base of the bipolar handswitch adapter shown in FIG. 5.
Figure 2:
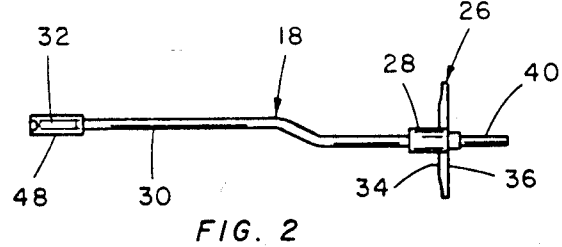
FIG. 2 is a top plan view of the bipolar handswitch adapter shown in FIG. 1.
Figure 5:
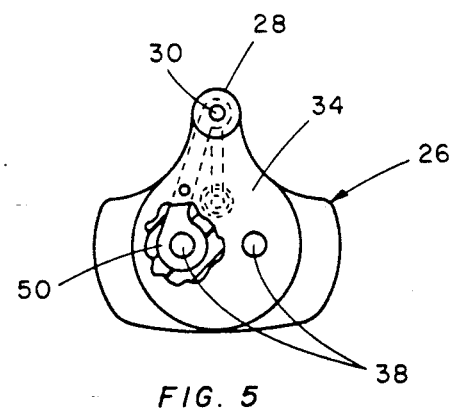
FIG. 5 is a sectional view of the base of the bipolar handswitch adapter shown in FIG. 2.
Figure 3:
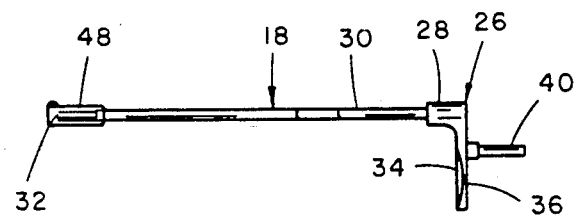
FIG. 3 is a side elevational view of the bipolar handswitch adapter shown in FIG. 1.
Figure 4:
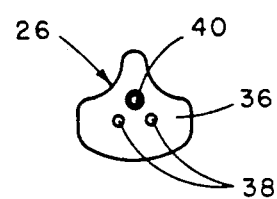
FIG. 4 is a bottom plan view of the base of the bipolar handswitch adapter shown in FIG. 2.

There is shown in the drawings the assembly of a Bipolar Forceps 10 and a handswitch adapter 18. The Bipolar Forceps 10 comprises a first tine or first blade portion 12, a second tine or second blade portion 14 and an instrument cup 16.

The Bipolar Forceps 10 may be formed by manufacturing the first and second tines 12, 14 of a conductive material such as stainless steel. The first and second tines 12, 14 function as a single or in line electrical conductors. Each of the tines 12, 14 has its terminal end remote from its tip 20 formed into a connector pin 22. In an overmolding step, the area adjacent the connector pins 22 is formed into the instrument cup 16. The connector pins 22 extend beyond the instrument cup 16. The instrument cup 16 is formed of an electrically insulating material. Under conditions where handswitching is not desired, the bipolar forceps 10 are connected to an electrosurgical generator 24 through the connector pins 22. The connector pins 22 are engaged to a socket (not shown) having a wire assembly that is then engaged to a electrosurgical generator by a male connector (not shown), for example.

If it is desired that the Bipolar Forceps 10 operate in a handswitch system, the hand switch adapter 18 is utilized. The hand switch adapter 18 comprises a handswitch adapter base 26 formed of an electrically non-

2 conductive material. The handswitch adapter base 26 includes a tubular handswitch adapter connector 28 formed of an electrically nonconductive material, open at one end and extending from the handswitch adapter base 26 in integral right angle relation thereto as shown in FIG. . A coaxial, electrically conductive, wire like adapter extension 30 is press fitted into the open end of the handswitch adapter connector 28 and has a free end which includes a reed microswitch 32. The adapter extension 30 is in proximate, spaced, parallel relation with a portion of the first tine 12. The handswitch adapter base 26 has a front face 34 and a rear face 36. A pair of spaced through holes 38 and a terminal pin 40. The terminal pin 40 extends from the rear face 36 of the handswitch adapter base 26 in a direction opposite from that toward which the adapter extension 30 extends. In use the connector pins 22 are passed through the through holes 38 of the handswitch adapter base 26 from the front face 34 through the rear face 36 with the connector pins 22 extending beyond the rear face 36 in the same direction as the terminal pin 40 and in spaced relation therewith. A female connector 42 is attached to the end of a bipolar handswitch cord 44 whose other end is attached to a male connector 46. The connector pins 22 and the terminal pin 40 are engaged in the female connector 42 and the male connector 46 is engaged to the electrosurgical generator 24. The reed microswitch 32 is covered by a thin silicone sleeve 48. The handswitch adapter connector 28 continues the coaxial arrangement of the adapter extension 30. One of the movable contacts of the reed microswitch 32 is connected to the outer conductor of the coaxial arrangement of the adapter extension 30 and the other movable contact of the reed microswitch 32 is connected to the inner conductor of the coaxial arrangement of the adapter extension 30. Within the handswitch adapter base 26, the outside portion of the coaxial arrangement of the handswitch adapter connector 28 is connected to one of the holes 38 formed through the handswitch adapter base 26 by a brass jumper plate 50 and the inside portion of the coaxial arrangement of the handswitch adapter connector 28 is connected to the terminal pin 40 by a brass strap 52.

To activate the Bipolar Forceps 10, the operator presses on the reed microswitch 32 closing the reed microswitch 32 and electrically jumping one the first tine 12 and the terminal pin 40 this activates a circuit in the electrosurgical generator 24 which initiates a second high voltage circuit in the electrosurgical generator 24 causing current to flow in the first and second tines 12, 14 allowing the tips 20 to be utilized in a manner well know in the art. See the U.S. Patent to Kirwan, Pat. No. 4890610 issued Jan. 2, 1990.

What I claim is:

1. A handswitch adapter for use with bipolar forceps, the hand switch adapter comprising a handswitch adapter base and an adapter extension, the handswitch adapter base formed of an electrically nonconductive material and including a tubular handswitch adapter connector physically open at one end and extending from the handswitch adapter base in integral right angle relation thereto, the adapter extension being formed of a coaxial, electrically conductive material and engaged to the open end of the handswitch adapter connector, the adapter extension having a free end remote from the handswitch adapter connector, the free end including a reed microswitch, the reed microswitch being electrically connected to the adapter extension, the handswitch adapter base having a front face and a rear face, a pair of spaced through holes formed therethrough and a terminal pin extending from the rear face thereof in a direction opposite from that toward which the adapter extension extends, the handswitch adapter electrically connected to the terminal pin, the adapter extension having coaxial conductors, one of the conductors connected to the terminal pin, the other conductor connected to one of the through holes.

2. The combination of a handswitch adapter and bipolar forceps, the bipolar forceps comprising first and second tines formed of a conductive material, the first and second tines each having a tip and having a terminal end remote from its tip, each of the terminal ends formed into a connector pin, the first and second tines in substantially spaced relation to each other and connected adjacent the connector pins by an insulating instrument cup, the connector pins extending beyond the instrument cup, the hand switch adapter comprising a handswitch adapter base and an adapter extension, the handswitch adapter base formed of an electrically nonconductive material and including a tubular handswitch adapter connector physically open at one end and extending from the handswitch adapter base in integral right angle relation thereto, the adapter extension being formed of a coaxial, electrically conductive material and engaged to the open end of the handswitch adapter connector, the adapter extension having a free end remote from the handswitch adapter connector, the free end including a reed microswitch, the handswitch adapter base having a front face and a rear face, a pair of spaced through holes formed therethrough and a terminal pin extending from the rear face thereof in a direction opposite from that toward which the adapter extension extends, the connector pins extending through the holes formed in the handswitch adapter base in spaced, parallel relation with the terminal pin, the adapter extension in spaced relation to the first and second tines, the handswitch adapter electrically connected to the terminal pin, the adapter extension having coaxial conductors, one of the conductors connected to the terminal pin, the other conductor connected to one of the through holes.

* * * * *